US006932786B2

(12) United States Patent
Giacomelli et al.

(10) Patent No.: US 6,932,786 B2
(45) Date of Patent: Aug. 23, 2005

(54) METHOD AND DEVICE FOR MONITORING THE ACCESS TO THE CARDIOVASCULAR SYSTEM OF A PATIENT

(75) Inventors: Sara Giacomelli, Poggio Rusco (IT); Ivan Rossi, Poggi Rusco (IT); Enrico Canini, Mirandola (IT)

(73) Assignee: Gambro Hospal, Basel (CH)

( * ) Notice: Subject to any disclaimer, the term of this patent is extended or adjusted under 35 U.S.C. 154(b) by 527 days.

(21) Appl. No.: 09/914,348
(22) PCT Filed: Dec. 22, 2000
(86) PCT No.: PCT/IB00/01954

§ 371 (c)(1),
(2), (4) Date: Dec. 21, 2001

(87) PCT Pub. No.: WO01/47581

PCT Pub. Date: Jul. 5, 2001

(65) Prior Publication Data
US 2003/0036719 A1 Feb. 20, 2003

(30) Foreign Application Priority Data
Dec. 28, 1999 (IT) .................................... TO99A001165

(51) Int. Cl.[7] ............................ A61M 37/00; C02F 1/44
(52) U.S. Cl. ...................... 604/6.08; 604/6.09; 604/6.1; 604/6.11; 210/645; 210/646
(58) Field of Search ............................... 604/5.04, 4.01, 604/6.06, 6.08, 6.09–6.11, 6.16, 67, 65, 5.01; 210/645–646, 103, 85, 87; 73/861.08; 422/44

(56) References Cited

U.S. PATENT DOCUMENTS

| 3,867,688 | A | * | 2/1975 | Koski ........................ 324/445 |
| 4,661,093 | A | | 4/1987 | Beck et al. ................... 604/50 |
| 5,510,717 | A | * | 4/1996 | Buffaloe et al. ............ 324/445 |
| 5,644,240 | A | * | 7/1997 | Brugger ....................... 324/439 |
| 5,685,240 | A | * | 11/1997 | Briggs et al. ............... 110/106 |
| 6,663,585 | B1 | * | 12/2003 | Ender ......................... 604/6.08 |

FOREIGN PATENT DOCUMENTS

| FR | 2067572 | 8/1971 |
| WO | WO 9912588 | 3/1999 |
| WO | WO 9924145 | 5/1999 |

* cited by examiner

Primary Examiner—Angela D. Sykes
Assistant Examiner—Leslie R. Deak
(74) Attorney, Agent, or Firm—Finnegan, Henderson, Farabow, Garrett & Dunner, L.L.P.

(57) ABSTRACT

A device for monitoring the access to the cardiovascular system of a patient undergoing an extracorporeal treatment of blood in a machine (1) comprising a treatment device (4) and an extracorporeal circuit (2), comprises: a voltage generator (16) for generating a potential difference between a part of the machine (1) and a first point (B) of a venous branch (8) of the extracorporeal circuit (2), connecting the patient to the treatment device (4); a detector (17) for detecting the value (dV) of a quantity that correlates with the electric current along at least one section (10a; 10b; 10c) of the venous branch (10) between the first point (B) and a venous needle (13) fitted at the end of the venous branch (8) and inserted in the vascular system of the patient (P); calculating means (15) for comparing the detected value (dV) with a reference range (I).

27 Claims, 2 Drawing Sheets

METHOD AND DEVICE FOR MONITORING THE ACCESS TO THE CARDIOVASCULAR SYSTEM OF A PATIENT

The present invention relates to a method and a device for monitoring the access to the cardiovascular system of a patient undergoing an extracorporeal treatment of blood.

The invention is useful in any kind of treatment in which blood is continuously withdrawn from a patient, circulated and treated in a treatment device, and returned, once treated, to the patient. Hemodialysis, hemofiltration, apheresis and plasmapheresis are examples of such treatment.

For the sake of clarity, the invention will be described hereunder in relation to a specific treatment, hemodialysis, to which however it is not limited as will readily appear to the persons skilled in the art.

A dialysis machine generally comprises.

a filter (hemodialyzer) having a first and a second compartments separated from one another by a semipermeable membrane;

an extracorporeal blood circuit, having an arterial branch connected to an inlet of the first compartment and a venous branch connected to an outlet of the first compartment; a blood pump is arranged on the arterial line and a bubble trap is connected to the venous line;

an dialysis liquid circuit, having an fresh dialysis liquid supply branch connected to an inlet of the second compartment and a used liquid branch connected to an outlet of the second compartment.

In use, the blood of the patient and the dialysis liquid are respectively circulated in the first and the second compartments, generally in counterflow.

During a dialysis treatment, undesirable substances (by-products of the metabolism, such as urea, creatinine, etc.) contained in the blood migrate across the semipermeable membrane from the blood compartment to the dialysis liquid compartment by diffusion (dialysis phenomenon, strictly speaking) and also generally by convection, a fraction of plasma water being usually filtered during the treatment so that the patient looses a few kilograms (so-called "weight loss") corresponding to an excess of water accumulated in the body between two treatment sessions.

Each branch of the extracorporeal circuit is fitted with a needle (respectively, arterial needle and venous needle), by means of which the extracorporeal circuit is connected to the patient: just before starting the treatment, the arterial needle and the venous needle are inserted in the fistula of the patient (portion of a vein surgically connected to an artery) for respectively collecting the blood to be treated and returning the treated blood to the patient's cardiovascular system.

Disconnection of one of the aforementioned needles from the fistula causes interruption of access to the patient's cardiovascular system. Disconnection of the venous needle, if not detected in time, has particularly serious consequences, as it can cause exsanguination of the patient. For this reason there have been various attempts to provide methods capable of detecting disconnection of the needles, and especially of the venous needle.

One of these methods, which is based on the electrical conductivity of the blood, is described in WO 99/12588. According to this method, the extracorporeal circuit and the patient's cardiovascular system are subjected to an electric current, and changes in the current that are caused by the disconnection of one of the needles or both of the needles is detected, by means of measuring instruments arranged along the extracorporeal circuit. The measuring instrument used are inductive couplers, i.e. coils arranged at predetermined locations along the extracorporeal blood circuit.

The method described above has various drawbacks. In particular, although valid from the theoretical standpoint, this method is not able to provide satisfactory results from the practical standpoint, because the high electrical impedance caused by the peristaltic pump, which in fact interrupts the continuity of blood flow, necessitates operating with relatively high currents in order to make use of the scant conductivity of the materials of which the extracorporeal circuit, the dialyzer, the hose of the peristaltic pump and the bubble trap are made (PVC, polycarbonate). The use of relatively high currents is certainly not advisable in a machine connected to a patient and even if they were used, it would not be possible to transmit these high currents by means of an inductive coupler which, among other things, also generates parasitic currents which disturb the measurement. In some dialysis machines the bubble trap also represents a high impedance of the same order of magnitude as the peristaltic pump, and thus makes one of the drawbacks previously described even more acute.

Therefore, in view of the fact that it is advisable to operate with relatively low currents and that the impedance of the peristaltic pump, and in the majority of cases, of the bubble trap, is high, it follows that disconnection of one of the needles causes only slight changes in current, such as could be confused with the background noise of the measuring instrument.

Furthermore, this method does not take into account that the patient might be connected to earth and that the dialyzer itself is in fact connected to earth, since the dialysis fluid circuit is connected to earth in accordance with the provisions of the safety standards relating to dialysis machines.

The aim of the present invention is to provide a method that obviates the drawbacks of the prior art.

According to the present invention, a method is provided for monitoring the access to the cardiovascular system of a patient undergoing an extracorporeal treatment of blood in a machine comprising a treatment device and an extracorporeal circuit having an arterial branch and a venous branch, the arterial branch having a first and fitted with an arterial needle to be inserted in the vascular system of the patient and a second end connected to an inlet of the treatment device, and the venous branch having a first end connected to an outlet of the treatment device and a second end fitted with an venous needle to be inserted in the vascular system of the patient, the method being characterized in that it comprises the steps of:

generating a potential difference between a first point of the venous branch and a part of the machine;

detecting the value (dV) of a quantity that correlates with the electric current along at least one section of the venous branch between the first point (B) and the venous needle; and comparing the detected value (dV) with a reference range (I).

The present invention relates, in addition, to a monitoring device.

According to the present invention, a device is provided for monitoring the access to the cardiovascular system of a patient undergoing an extracorporeal treatment of blood in a machine comprising a treatment device and an extracorporeal circuit having an arterial branch and a venous branch, the arterial branch having a first end fitted with an arterial needle to be inserted in the vascular system of the patient and a second end connected to an inlet of the treatment device, and the venous branch having a first end connected to an outlet of the treatment device and a second end fitted with an venous needle to be inserted in the vascular system of the patient, the device being characterized in that it comprises:

a voltage generator for generating a potential difference between a first point (B) of the venous branch and a part of the machine;

a detector for detecting the value (dV) of a quantity that correlates with the electric current along at least one section of the venous branch between the first point (B) and the venous needle;

calculating means for comparing the detected value (dV) with a reference range (I).

The invention will now be described, with respect to the appended drawings, in which.

Figure 1:
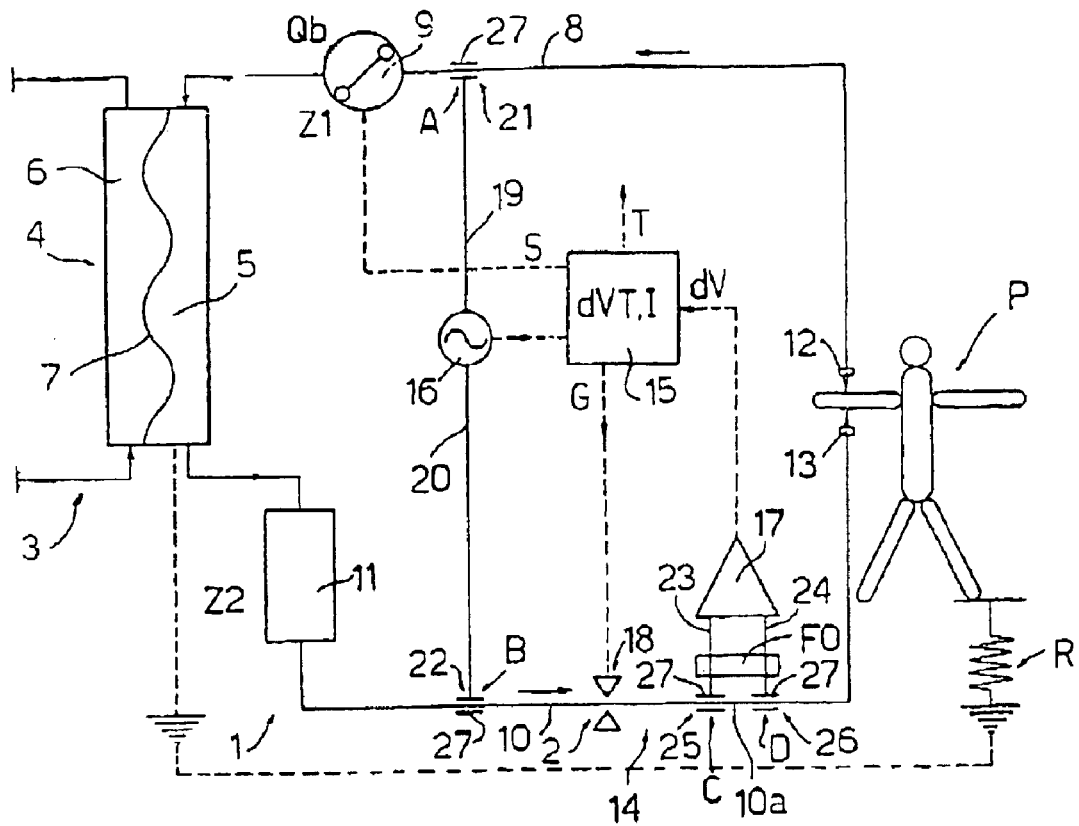
FIG. 1 is a schematic representation of a dialysis machine connected to a patient and equipped with a monitoring device according to the invention.
Figure 2:
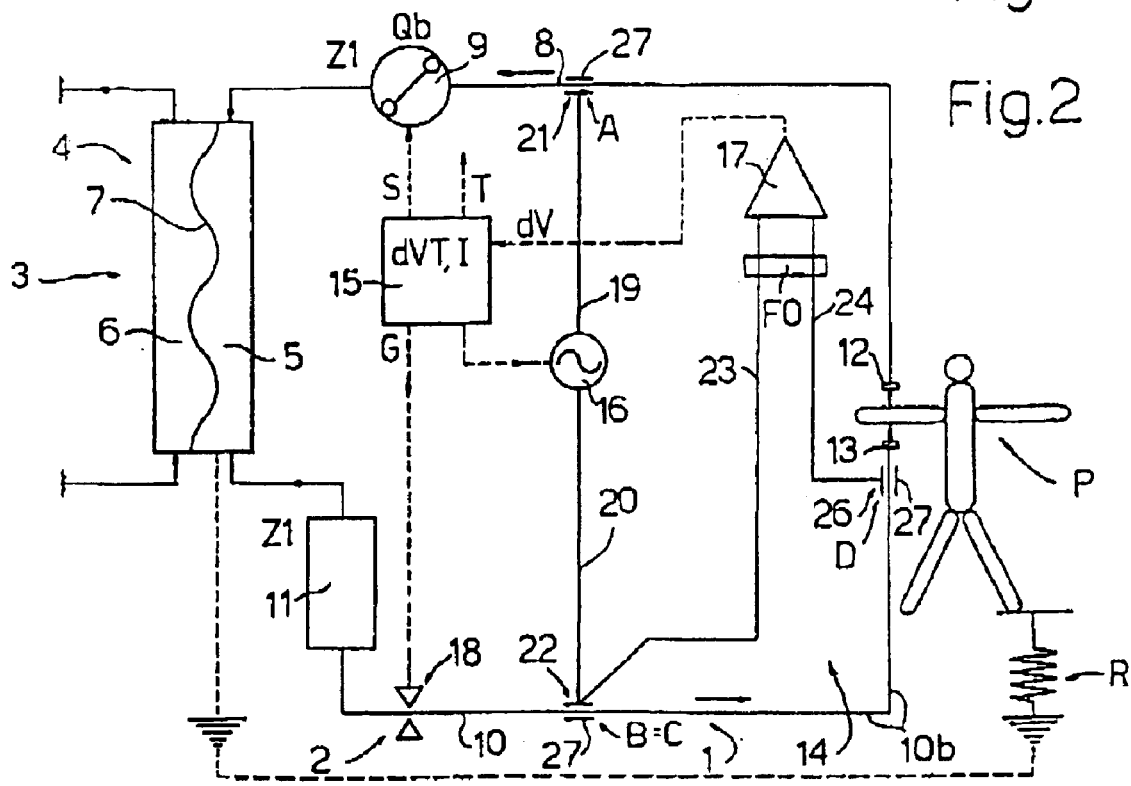
FIG. 2 is a schematic representation of a dialysis machine connected to a patient and equipped with a variant of the device in FIG. 1.
Figure 3:
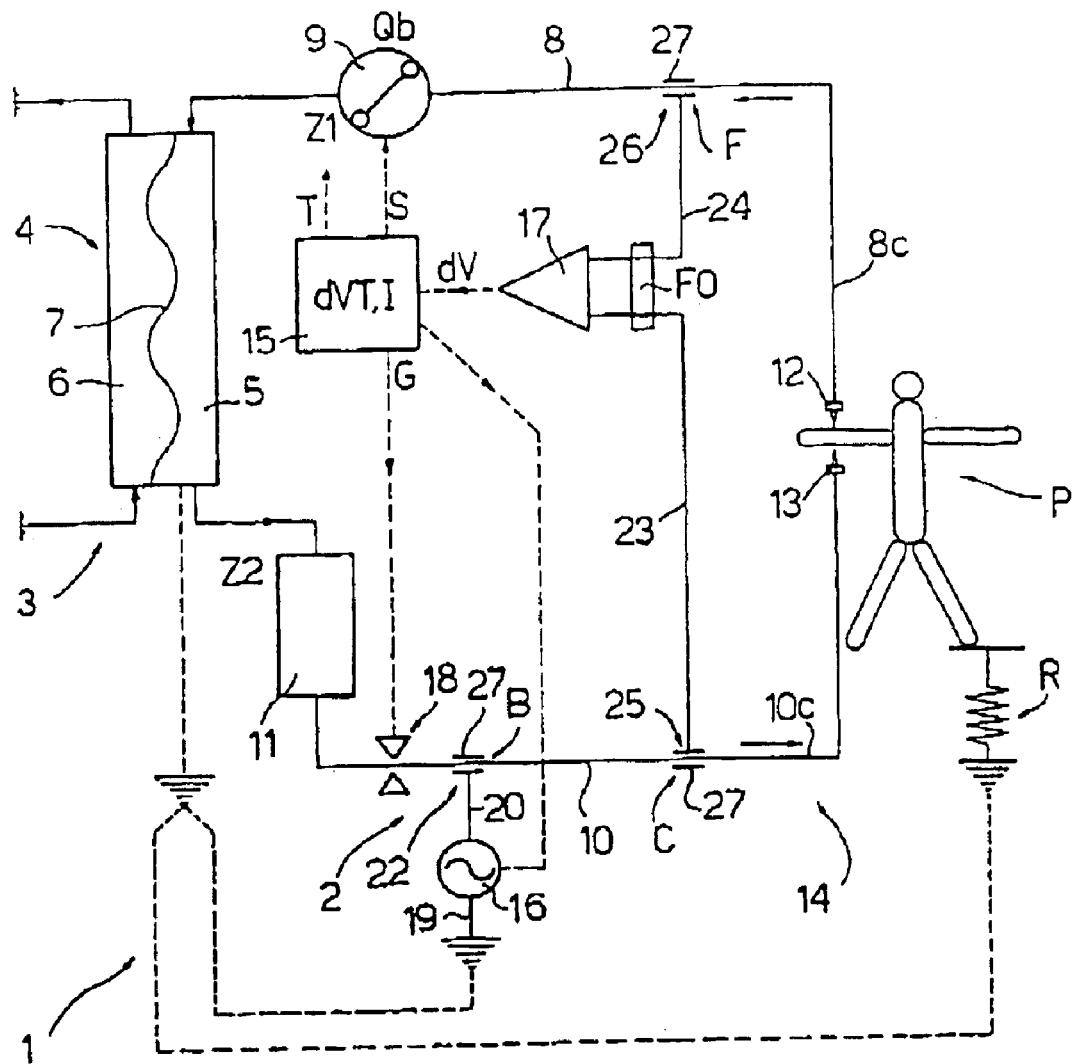
FIG. 3 is a schematic representation of a dialysis machine connected to a patient and equipped with another variant of the device in FIG. 1.

In FIGS. 1, 2 and 3, the number 1 indicates a dialysis machine connected to a patient P. The machine 1 comprises an extracorporeal blood circuit 2 and a dialysis fluid circuit 3 which pass through a dialyzer 4, which comprises a blood compartment 5 and a dialysis compartment 6 separated by a semipermeable membrane 7.

The extracorporeal blood circuit 2 comprises, in addition to the compartment 5 of dialyzer 4, an arterial branch 8, along which a peristaltic pump 9 is arranged, supplying a blood flow $Q_b$, and a venous branch 10, to which a bubble trap 11 is connected. Arterial branch 8 has a needle 12 which, in use, is inserted in a fistula of patient P to collect blood from the cardiovascular system of the patient P, while venous branch 10 has a venous needle 13 which, in use, is inserted in the fistula for returning the treated blood to the cardiovascular system of patient P. Arterial and venous branches 8 and 10 are tubes made of a plastic material, generally PVC, as well as bubble trap 11. Dialyzer 4 is also made of plastic material, the housing of it generally of polycarbonate.

In FIGS. 1, 2 and 3, machine 1 is equipped with a device 14 for detecting disconnection of needles 12 and 13. The principle of the device 14 is based on the electrical conductivity of the blood and on data found experimentally that showed that circuit 2 made of PVC can be regarded as an insulator and that both the peristaltic pump 9 and the bubble trap 11 can be regarded as concentrated impedances designated Z1 and Z2 respectively. Peristaltic pump 9 cyclically interrupts the blood flow $Q_b$, at each half-turn of the pump 9 and accordingly the impedance Z1 is a function of the number of turns of pump 9 and of the supply frequency. Experiments have established that the impedance Z1 is between 500 and 2000 kΩ. The impedance Z2 is determined as well by the fact that the blood flow $Q_b$ is interrupted in the bubble trap 11 and the value assumed by Z2 is also between 500 and 2000 kΩ. Recent designs of bubble trap have a relatively low impedance, which is negligible with respect to the impedance Z1. This circumstance will be borne in mind when describing the operation of device 14.

The impedances of the other compartments of extracorporeal circuit 2 are negligible with respect to the values of impedance Z1. To evaluate the operation of device 14, it is necessary to bear in mind that the dialyzer 4 is connected to earth via the dialysis fluid circuit 3 and that the patient P may be connected to earth (R=0) or insulated (R=infinity) or in a situation intermediate between the two preceding limiting situations. These distinctions are important as it would be difficult to prevent the patient P from moving, for example resting a foot on the floor or placing a hand on the bedhead of an uninsulated bed, thus altering the configuration of the possible electric circuits defined by the machine 1, the patient P, and device 14.

In FIG. 1, device 14 comprises a control unit 15, a generator 16 connected to arterial and venous branches 8 and 10, a detector 17 of a voltage drop and a clamp 18 arranged along venous branch 10. Generator 16 is connected respectively by two conductors 19 and 20 and by two capacitive couplers 21 and 22 respectively to arterial branch 8 and to venous branch 10. Detector 17 is connected by two conductors 23 and 24 and by two capacitive couplers 25 and 26 to venous branch 10 for detecting the voltage drop along a predetermined section 10a of branch 10. An optimum filter FO is arranged along conductors 23 and 24 for minimizing the effect of noise on the input of detector 17, which is connected to control unit 15 for transmitting a value dV indicating the voltage drop in section 10a to unit 15, which compares this value with a threshold value dVT. If the value detected is not inside a range I around the threshold value dVT, control unit 15 emits a control signal S for stopping pump 9, a control signal G for closing clamp 18 and a signal T for emitting a visible and/or acoustic alarm signal.

Capacitive couplers 21, 22, 25 and 26 are made with respective metal tubes 27, which are connected to the respective conductors 19, 20, 23 and 24 and are arranged around portions of the respective PVC tubes. From the electrical standpoint, tube 27 defines a first plate of a capacitor, the PVC tube defines the dielectric, and the blood inside the PVC tube defines the second plate.

Capacitive coupler 21 is arranged on arterial branch 8 at a point A between the arterial needle 12 and the peristaltic pump 9, while capacitive coupling 22 is arranged on the arterial branch 10 at point B between bubble trap 11 and needle 13. Detector 17 is connected to venous branch 10 at points C and D, both of which are between point B and the venous needle 13 and define the end of section 10a.

When the patient is insulated (R infinite) and impedance Z2 is high, the operation of the monitoring device 14 according to the invention is as follows: the blood being circulated in the extracorporeal circuit 2 in the direction indicated by the arrows in FIG. 1, a potential difference is applied between venous branch 10 and arterial branch 8 by means of generator 16 and the respective capacitive couplers 21 and 22. This potential difference generates a current between a section of venous branch 10 and a section of arterial branch 8 which is closed by the cardiovascular system of the patient P on account of the high impedances Z1 and Z2 on the other portion of circuit 2. Detector 17 detects the voltage drop along section 10a of arterial branch 10 and stores a value indicating the voltage drop as threshold value dVT, determines the range I of acceptability around the threshold value dVT and checks whether the successive values dV are inside range I.

When one of the needles 12 and 13 accidentally becomes disconnected from the fistula, the detector 17 detects the cancellation of the voltage drop dV in section 10a, and the control unit 15 emits signals S, G and T for stopping the peristaltic pump 9, closing the clamp 18, and emitting an alarm signal.

The monitoring device 14 is particularly advantageous because it by-passes the impedance Z1 and Z2, and the dialyzer 4 which is connected to earth. Therefore it is possible to work with relatively low currents since disconnection of one of the needles 12 and 13 represents an appreciable change in the current along a circuit comprising a portion of the arterial branch 8 and a portion of the venous branch 10, the conductors 19 and 20 and the cardiovascular system of the patient P.

When the patient P is connected to earth (R=0), if the venous needle 13 becomes disconnected, there is no current flowing through the venous branch 10 and therefore detector 17 detects a voltage drop equal to zero as is the case when patient P is insulated. If the arterial needle 12 becomes disconnected, there is a voltage drop in section 10a, which is a function of the impedance Z1 of the peristaltic pump and is therefore significant owing to the high value of impedance Z1.

When Z2 is negligible, disconnection of venous needle 13 is detected both when the patient is insulated (R infinite) and when he is connected to earth (R=0), as preferential flow of current occurs along the portion of extracorporeal circuit 2 on the side of patient P.

In the embodiment of FIG. 2, there is no capacitive coupler 25 since point C coincides with point B, whereas point D is located close to the venous needle 13. In this case, detector 17 detects the change in voltage along a section 10b, which is a section of branch 10 between point B (i.e. C) and, essentially, the venous needle 13.

When the patient P is insulated (R infinite) and Z2 is high, the current circulates through conductors 19 and 20, a portion of the venous branch 10 and a portion of the arterial branch 8. Disconnection of one of the needles 12 and 13 has the effect that the voltage drop is cancelled along the section 10b and the patient P.

When the patient P is connected to earth (R=0), a disconnection of the venous needle 13 causes the cancellation of the voltage drop as in the proceding case, whereas when the arterial needle 12 is disconnected, the voltage drop becomes a function of the impedance Z1 as in the preceding case.

When Z2 is negligible, the considerations relating to the variant in FIG. 1 apply, except that the greater length of section 10b relative to section 10a makes it possible to refer to high values dV, at equal current passing through the venous branch 10, and therefore the device 14 is more efficient, as it increases the difference between the value of the voltage drop dV determined by the condition with the venous needle 13 connected and the zero value of dV.

According to a variant that is not shown, again the capacitive coupler 26 is omitted and is replaced with a conductive bracelet, not shown, connected directly to one wrist of the patient P. The operation of the said variant that is not shown does not differ substantially from the variant in FIG. 2.

According to the variant in FIG. 3, capacitive coupling 21 to the arterial branch 8 is omitted, since generator 16 is connected to earth via conductor 19, and detector 17 is connected to the venous branch 10 via conductor 23 and the capacitive coupler 25 at point C and to the arterial branch 8 via conductor 24 and the capacitive coupler 26 at a point F between the peristaltic pump 9 and arterial needle 12.

In use, when the patient P is insulated (R infinite) and the impedance Z2 is high, the value dV of voltage drop along section 10c of the venous branch, section 8c of the arterial branch 8, and the cardiovascular system of the patient P is detected. Section 10c is between point C and arterial needle 13, whereas section 8c is between point F and venous needle 12. Disconnection of one of the needles 12 and 13 causes cancellation of the voltage drop.

When the patient P is connected to earth (R=0), a disconnection of the venous needle 13 causes the cancellation of the voltage drop, whereas a disconnection of the arterial needle 12 does not cause any appreciable change in the voltage drop dV.

When the impedance Z2 is negligible, a low current will pass along section 10c, however section 10c along which the voltage drop dV is determined is relatively long and therefore a detection thereof is significant.

In practice, all the variants of the monitoring device 14 described with reference to the FIGS. 1, 2 and 3 enable a reliable detection of the disconnection of the venous needle 13, since a disconnection of the venous needle 13 causes, both when the patient P is insulated (R infinite), and when the patient is connected to earth (R=0), a significant change in the value dV of voltage drop, in comparison with the situation in which the venous needle 13 is connected.

What is claimed is:

1. A method of monitoring a cardiovascular access during an extracorporeal blood treatment, comprising the steps of:

providing an extracorporeal blood circuit comprising an arterial branch and a venous branch, the arterial branch connecting an arterial needle inserted into a patient to an inlet of a blood treatment device, the venous branch connecting an outlet of the blood treatment device to a venous needle inserted into a patient;

providing a conductive connection between the arterial branch and the venous branch, said conductive connection having first and second connection locations, wherein said first connection location is located upstream of the blood treatment device and said second connection location is located downstream of said blood treatment device;

circulating blood in the extracorporeal blood circuit;

generating a potential difference between the arterial branch and the venous branch;

detecting a value of a quantity corresponding to an electric current along at least one portion of the venous branch, said at least one portion being between the conductive connection and the venous needle; and comparing the detected value to a reference range.

2. A method according to claim 1, wherein an end of the conductive connection is located on the venous branch between the venous needle and a bubble trap, said bubble trap being connected to the venous branch.

3. A method according to claim 1, wherein an end of the conductive connection is located on the arterial branch between the arterial needle and a peristaltic pump arranged on the arterial branch.

4. A method according to claim 1, wherein said quantity corresponding to an electric current is a voltage drop.

5. A method according to claim 1, wherein a capacitive coupler connects the conductive connection to the arterial branch.

6. A method according to claim 1, wherein a capacitive coupler connects the conductive connection to the venous branch.

7. A method according to claim 1, wherein a detector circuit is provided on said conductive connection, said detector circuit being configured to perform said detecting of the value.

8. A method according to claim 1, wherein a generator circuit is provided on said conductive connection, said generator circuit being configured to perform said generating the potential difference.

9. A method in accordance with claim 1, wherein a detector circuit is configured to perform said detecting the value, said detector circuit being connected to the venous branch at first and second points, said first and second points being located on said at least one portion of the venous branch.

10. A method according to claim 9, wherein a first capacitive coupler connects the detector circuit to the venous branch at said first point, and a second capacitive coupler connects the detector circuit to the venous branch at said second point.

11. A method according to claim 1, wherein a generator circuit generates the potential difference, said generator circuit being connected to earth.

12. A device for monitoring a cardiovascular access during an extracorporeal blood treatment comprising:
   a conductive connection arranged between a first passage point of an arterial branch of an extracorporeal blood circuit, and a second passage point of a venous branch of the extracorporeal blood circuit;
   a voltage generator circuit configured to generate a potential difference between said first and second passage points when the extracorporeal blood circuit is connected to a patient through an arterial needle and a venous needle;
   a detector circuit configured to detect a value of a quantity corresponding to an electric current along at least one section of the extracorporeal circuit, said at least one section of the extracorporeal circuit comprising:
      a portion of the venous branch between the second passage point and the venous needle;
      a portion of the arterial branch between the arterial needle and the first passage point; and
      the conductive connection; and
   a comparator circuit configured to compare the value to a reference range.

13. A device according to claim 12, comprising an extracorporeal blood circuit having a first point of an arterial branch located at the first passage point, and a second point of a venous branch located at the second passage point.

14. A device according to claim 13, wherein said second point is located between the venous needle and a bubble trap, said bubble trap being arranged along the venous branch.

15. A device according to claim 13, wherein said first point is located between the arterial needle and a peristaltic pump, said peristaltic pump being arranged on the arterial branch.

16. A device according to claim 12, wherein a capacitive coupler is arranged substantially on said first passage point.

17. A device according to claim 12, wherein a capacitive coupler is arranged substantially on said second passage point.

18. A device according to claim 16 or 17, wherein the capacitive coupler comprises at least one metal tube, said metal tube being wound around a respective portion of the extracorporeal blood circuit.

19. A device according to claim 12, wherein the detector circuit is arranged substantially on the conductive connection.

20. A device according to claim 12, wherein the voltage generator circuit is arranged substantially on the conductive connector.

21. A device according to claim 12, wherein the detector circuit is connected to the venous branch at a first connection point and a second connection point, said first and second connection points being located on said portion of the venous branch between the second passage point and the venous needle.

22. A device according to claim 12, wherein the voltage generator circuit is connected to earth.

23. A device according to claim 12, wherein the detector circuit is a voltage drop detector.

24. A device according to claim 12, wherein the comparator circuit is configured to output at least one control signal when the value is outside the reference range.

25. A device according to claim 12, further comprising at least one capacitive coupler, said at least one capacitive coupler being connected to the voltage generator circuit and the extracorporeal blood circuit.

26. A device according to claim 12, further comprising at least one capacitive coupler, said at least one capacitive coupler being connected to the detector circuit and the extracorporeal blood circuit.

27. A device according to claim 12, wherein the voltage generator circuit is connected to the extracorporeal blood circuit and the voltage generator circuit is also connected to earth.

* * * * *